United States Patent [19]

Rambow

[11] Patent Number: 5,031,467
[45] Date of Patent: Jul. 16, 1991

[54] PULSE ECHO TECHNIQUE FOR DETECTING FLUID FLOW

[75] Inventor: Frederick H. K. Rambow, Houston, Tex.

[73] Assignee: Shell Oil Company, Houston, Tex.

[21] Appl. No.: 448,446

[22] Filed: Dec. 11, 1989

[51] Int. Cl.$^5$ .................. G01F 1/66; G01N 29/02; E21B 14/10

[52] U.S. Cl. ................... 73/861.25; 73/155; 340/606; 367/93

[58] Field of Search .......... 73/861.25, 155, 40.5 A, 73/592, 861.04; 340/606, 608, 621; 128/661.08; 367/86, 89, 30, 93

[56] References Cited

U.S. PATENT DOCUMENTS

| | | | |
|---|---|---|---|
| 3,369,626 | 2/1968 | Zemanek, Jr. | 181/0.5 |
| 3,776,032 | 12/1973 | Vogel | 73/155 |
| 4,744,367 | 5/1988 | Kodama et al. | 73/861.25 X |
| 4,790,321 | 12/1988 | Miwa et al. | 73/861.25 X |
| 4,803,990 | 2/1989 | Bonnefous et al. | 73/861.25 X |
| 4,944,189 | 7/1990 | Nakajima et al. | 73/861.25 |

Primary Examiner—Charles A. Ruehl

[57] ABSTRACT

A method and apparatus for detecting fluid flow behind an acoustically reflective structure using pulse echo techniques which do not depend upon measurement of a Doppler effect. A transducer is provided for generating a high frequency beam of acoustical energy in the form of pulses. The transducer is placed proximate, preferably adjacent, the reflective structure such that the acoustic beam is directed toward such structure. A transducer is also provided for detecting the acoustic reflections of the pulses, proximate the position from which the pulses originated, and generating corresponding electrical signals. An electric circuit is provided for subtracting a pair of acoustic reflection signals separated by a short interval of time to produce a difference signal from which the presence or absence of fluid flow behind the acoustically reflective surface can be determined. In the preferred embodiment, a preselected number of the difference signals are "stacked" by adding the absolute values of such signals to produce a "stacked" signal trace which is more susceptible to evaluation, especially for determination of relative flow velocities.

12 Claims, 4 Drawing Sheets

FIG.C

PULSE ECHO TECHNIQUE FOR DETECTING FLUID FLOW

BACKGROUND OF THE INVENTION

The present invention relates generally to a method and apparatus for using pulse echo techniques to detect fluid flow behind an acoustically reflective structure. More particularly, it relates to a method for detecting fluid flow behind casing in a borehole.

The use of pulse echo techniques in the borehole environment is not new. The use of a variety of devices employing such techniques for the evaluation of formations that are penetrated by a borehole in the search for hydrocarbon deposits is well known. Many such devices have been referred to generically as "borehole televiewers" (BHTVs). The leading reference in this field of science and technology is U.S. Pat. No. 3,369,626 entitled "METHOD AND APPARATUS FOR PRODUCING A VISUAL RECORD OF PHYSICAL CONDITIONS OF MATERIALS TRAVERSED BY A BOREHOLE," issued on Feb. 20, 1968 to J. Zemanek, Jr. Since the issuance of this patent, numerous patents and technical papers pertaining to this field have been published. Accordingly, a further description of the art is deemed unnecessary at this time.

Although pulse echo techniques which involve measurement of the Doppler effect have been used for years to measure flow velocities, they are effective only when the flow being measured has a velocity component which is parallel to the acoustic beam transmitted by the device in use; they are ineffective when the transmitted acoustic beam is perpendicular to the flow velocity. Further, such devices have been ineffective in measuring flow behind an acoustically reflective barrier, e.g., casing in a borehole, essentially because of the magnitude of the acoustic return from the reflective barrier.

In the exploration and production of hydrocarbons, boreholes are normally "cased" prior to completion of a well by installing a tubular casing in the borehole which is cemented into place by cement which is disposed between the casing and the wall of the borehole. It is desirable to be able to detect and measure fluid flow behind the casing, i.e., between the casing and the wall of the borehole. It will be noted that, as used herein, "fluid flow" refers to the flow of liquids, gases, or a combination of both. Obviously, it is advantageous to be able to accomplish this objective with a method that includes the use of a tool that can be deployed through the central bore of the casing.

SUMMARY OF THE INVENTION

In accordance with a preferred embodiment of the present invention, a method is provided for detecting and measuring the velocity of fluid flow behind an acoustically reflective structure, e.g., the casing of a borehole, using pulse echo techniques. The method comprises the placement of a transmitting/receiving transducer proximate the reflective structure. The transducer generates a high frequency, on the order of 500 kHz and higher, beam of acoustic pulses that is projected toward and substantially perpendicular to the surface of the reflective structure. The acoustic reflections of a pair of such pulses, separated by a short interval of time, are detected and recorded in the form of signal traces. A subtraction of the two signal traces produces a difference signal trace which can be analyzed for the presence of fluid flow behind the reflective structure. In the preferred embodiment, means are provided for "stacking" the difference signal traces by summing the absolute values of a preselected number of the difference traces generated within a preselected short interval of time to produce a resultant trace which is more susceptible to analysis, and more particularly for determination of relative flow velocities at spaced intervals of time.

It is therefore a primary object of the present invention to provide a method for detecting fluid flow behind an acoustically reflective structure using pulse echo techniques.

Another object of the present invention is to provide a method of measuring the velocity of fluid flow behind an acoustically reflective structure using pulse echo techniques.

Another object of the present invention is to provide a method for detecting fluid flow behind casing in a borehole using pulse echo techniques.

Another object of the present invention is to provide a method for measuring the velocity of fluid flow behind casing in a borehole using pulse echo techniques.

Another object of the present invention is to provide a method for detecting and measuring the velocity of fluid flow behind an acoustically reflective structure using pulse echo techniques wherein the pulsed acoustic beam is substantially perpendicular to the direction of fluid flow.

An important advantage of the present invention is that the method does not depend upon the fluid flow which is being detected or measured producing detectable sonic energy as is the case in prior art "noise logs."

These and other objects and advantages of the present invention will no doubt become apparent to those skilled in the art after having read the following detailed description of the preferred embodiment which are contained in and illustrated by the various drawing figures.

BRIEF DESCRIPTION OF THE DRAWINGS

FIG. 1A is a block diagram of a portion of FIG. 1 showing the use of separate transmitter and receiving transducers.

FIGS. 6A through 6D illustrate the "stacked" signals recorded in different accumulators, where the time interval "T" between the pulses generated to obtain the difference signals which are "stacked" is a different value, as more completely explained in the detailed description of the invention which follows, for each accumulator.

DETAILED DESCRIPTION OF THE PREFERRED EMBODIMENT

Figure 1:
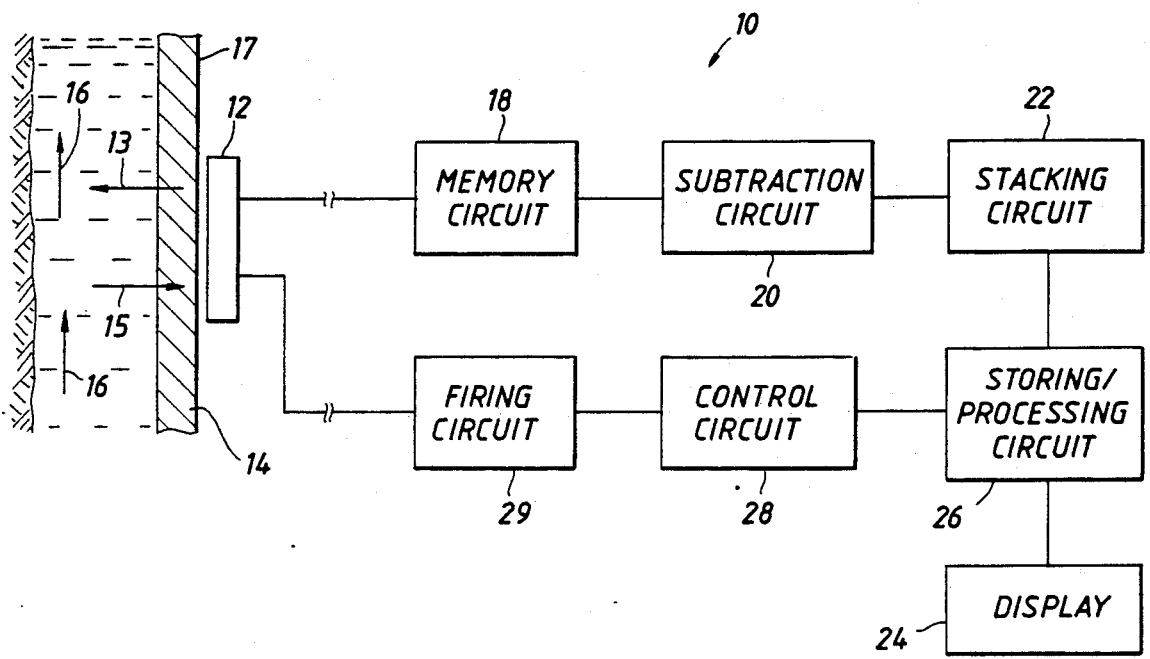
FIG. 1 is a block diagram of an apparatus for detecting fluid flow behind an acoustically reflective structure constructed in accordance with the present invention.

In accordance with a preferred embodiment of the present invention, a method and apparatus are provided for detecting and determining the relative velocity of fluid flow behind an acoustically reflective structure, e.g., the casing of a borehole, using pulse echo techniques. The method of the present invention does not depend upon measurement of the Doppler effect, and, accordingly, can be used to detect and measure flow velocities which are substantially perpendicular to the pulsed beam of acoustic energy utilized by the invention. The apparatus 10 of the present invention is illustrated by the block diagram of FIG. 1. The method comprises placing transmitting/receiving ("pulse echo") transducer 12 proximate the acoustically reflective structure 14 having a first side 17 and an opposite second side 19. It will be appreciated by those skilled in the art that the transmitting/receiving transducer 12 can comprise a single unit as shown in FIG. 1, or, alternatively, can comprise separate transmitting 12A and receiving 12B transducers as shown in FIG. 1A. The transducer 12 generates a high frequency, generally on the order of 500 kHz or higher, pulsed beam of acoustic energy which is substantially perpendicular to the acoustically reflective surface. A firing circuit 29 is provided for driving the (pulse generating function of the) transducer 12. The direction of the generated acoustic beam is indicated by the arrow 13. A portion of the acoustic energy is reflected back to the transducer 12 off the reflective structure 14 and a portion is transmitted through the structure 14. The direction of the reflected acoustic energy is indicated by the arrow 15. Some of the energy which is transmitted through the reflective structure 14 will be reflected back by any material behind the reflective structure, including any fluids. When the material behind the reflective structure is stationary, two echo (reflected) signals—i.e., the signals generated by the receiver of the transducer 12 which are a function of the acoustic reflections of the acoustic pulses generated by the transducer 12—separated by a short time interval will be essentially identical. It will be appreciated by those skilled in the art that the transducer 12 also functions to detect the acoustic reflections and generate electrical signals which are proportionate to such acoustic reflections. When there is fluid flowing behind the reflective structure 14, indicated for illustration purposes in FIG. 1 by the arrows 16, small particles and/or bubbles in the flowing fluid scatter some of the energy out of the acoustic beam. Thus, with all parts of the system stationary except for fluid flowing behind the reflective structure 14, two echo signals separated by a short time interval will be essentially identical except for the portion of the signal that is randomly scattered by the flowing fluid behind the reflective structure 14. In light of the foregoing, it will be understood that some "scatterers," e.g., gas bubbles or nonhomogeneous particles, must be present in the fluid for flow to be detectable.

Accordingly, a pair of the signals generated by the receiving (detecting) section of the transducer 12, i.e., signals which are proportionate to the acoustic reflections of a pair of the generated acoustic pulses, separated by a short interval of time, are stored in a first electric circuit 18 as an amplitude vs. time signal trace. A second electric circuit 20 is provided for subtracting the signals stored in the previous step to produce a difference signal trace which is a function of the fluid flow behind the reflective structure. In the preferred embodiment, a third electric circuit 22 is also provided for "stacking" the difference signals by adding the absolute values of a preselected number of difference signal traces (amplitude plotted vs. time), generated by the electric circuit 22 within a preselected short interval of time, to produce a resultant trace which is more susceptible to analysis. A display 24 coupled to the electric circuit 22 is provided for displaying the stacked signal trace generated by the third electric circuit 22.

In the preferred embodiment, a fourth electric circuit 26 is provided for storing a preselected number of the stacked signal traces generated by the third electric circuit 22 at spaced intervals of time. The fourth electric circuit 26 is coupled to the display 24. The stored stacked signal traces can be compared to determine the relative velocities of the fluid flow behind the acoustically reflective surface 14.

EXAMPLE 1

Figure 2:
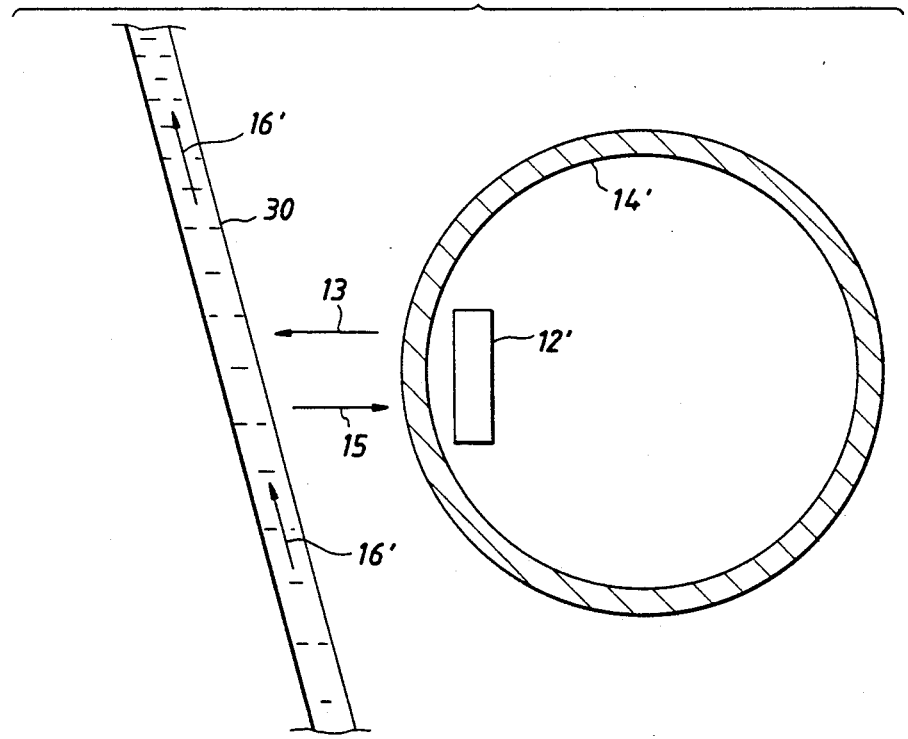
FIG. 2 is a diagram of the laboratory set-up of an experiment relating to the present invention as hereinafter described in detail under Example 1.

In a laboratory experiment, an acoustic transducer was placed inside a length of fiberglass casing (similar to that used in the petroleum industry for the casing of boreholes). A Tygon ™ plastic tube carrying a flowing fluid was placed outside and proximate the casing. FIG. 2 illustrates a schematic of the laboratory arrangement of the casing 14', transducer 12', and the Tygon ™ plastic tube 30. The primed reference numerals in FIG. 2 correspond to like numbered unprimed reference numerals in FIG. 1, representing equivalent elements.

The tube 30 was tilted at an arbitrary and variable angle with respect to the casing and was positioned at varying offsets from the casing.

Figure 3:
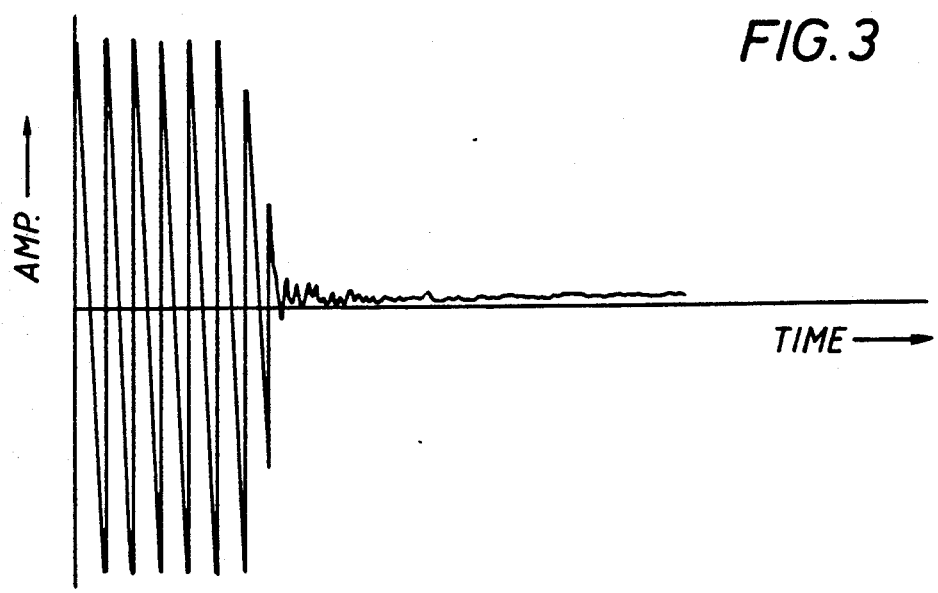
FIG. 3 illustrates a waveform of an acoustic reflection signal obtained in an experiment relating to the method of the present invention.

FIG. 3 illustrates a typical waveform from a single short pulse generated by the transducer with the transducer positioned as shown in FIG. 2. The acoustic reflection from the fiberglass casing and the multiples ("ringing effect") between the transducer and the casing dominate the signal. The early arriving peaks from these reflections are substantially off the scale of the plot in FIG. 3.

Figure 4A:
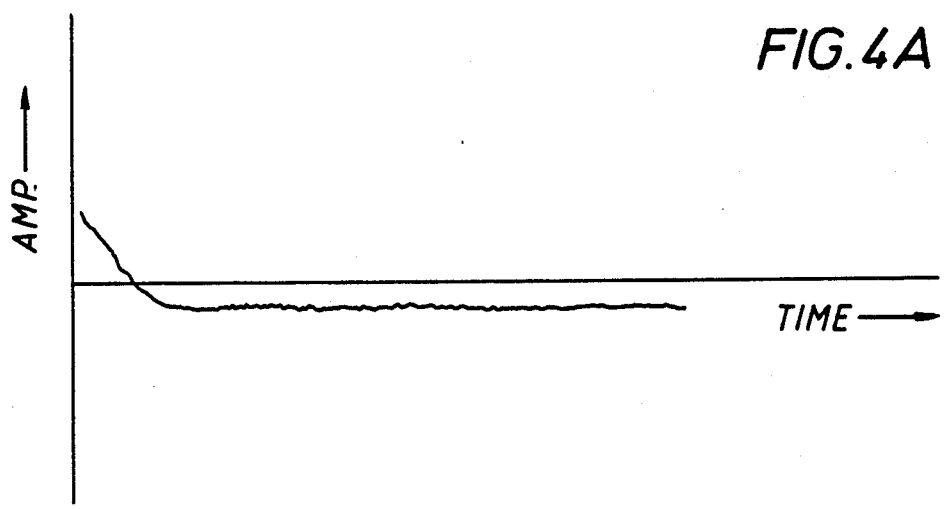
FIG. 4A illustrates a waveform depicting the result of the subtraction of two waveforms such as those shown in FIG. 3 which were obtained in an experiment relating to the method of the present invention, under "no flow" conditions as hereinafter described in detail.

FIG. 4A illustrates the result of the subtraction of two signals taken about one-half second apart with no flow in the plastic tube. The large acoustic reflection from the casing was essentially cancelled. The resulting signal trace was as near zero as the noise and stability of the system of the experiment allowed.

Figure 4B:
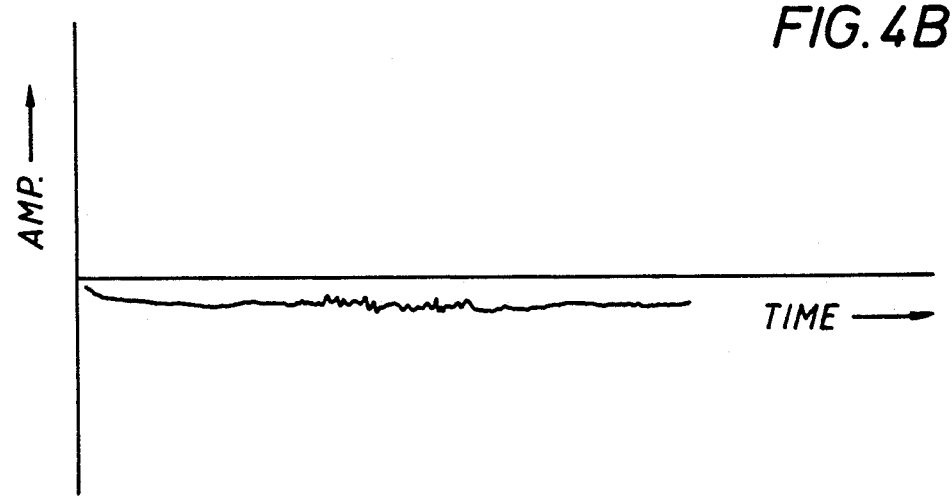
FIG. 4B illustrates a waveform of the type shown in FIG. 4A when fluid flow is detected as hereinafter described in detail.

FIG. 4B illustrates a typical subtraction of two signals taken about one-half second apart when there was flow in the plastic tube. The resulting time varying inhomogeneity in the flowing fluid created an incoherence between the signals that did not cancel.

Figure 5A:
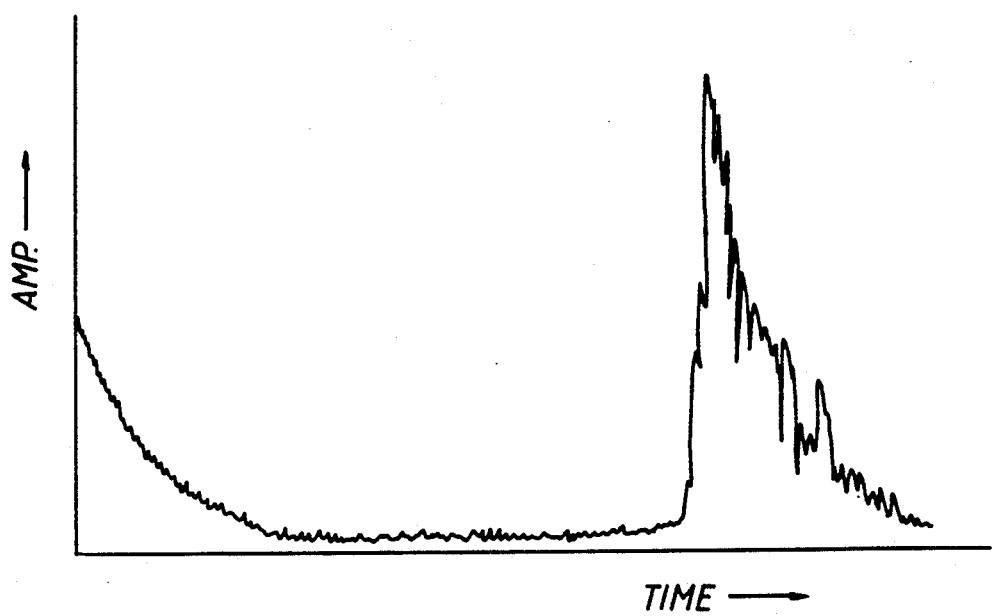
FIG. 5A illustrates a typical "stacking" of waveforms such as those illustrated in FIG. 4B in which flow is detected.
Figure 5B:
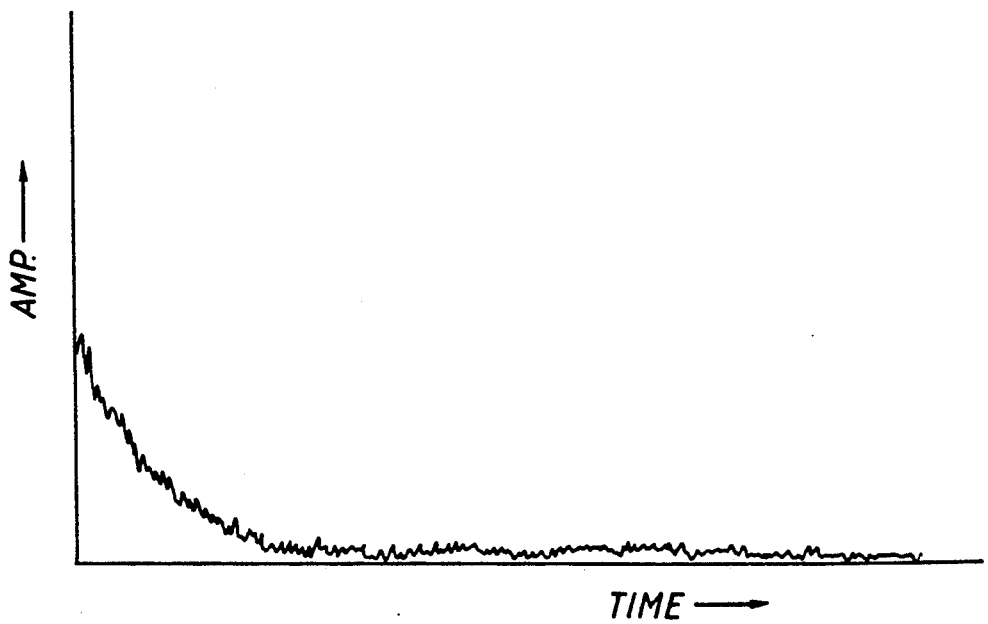
FIG. 5B illustrates a typical "stacking" of waveforms such as those illustrated in FIG. 4A under "no flow" conditions.
Figure 6A:
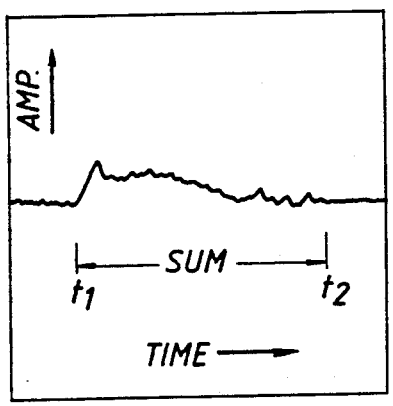
Figure 6B:
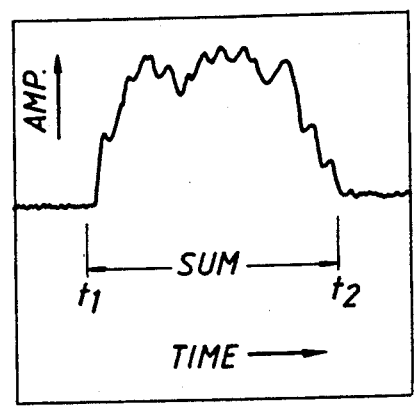
Figure 6B:
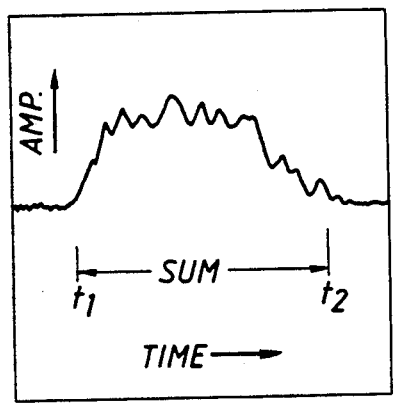
Figure 6D:
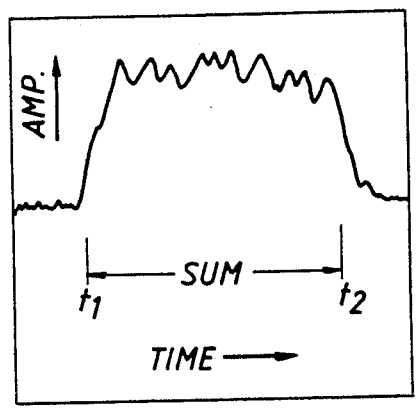

FIGS. 5A and 5B illustrate examples of "signal stacking." In this example, ten difference traces (such as those illustrated in FIG. 4B) were "stacked" by summing the absolute values of the difference traces. FIG.

5A illustrates the stacked signal trace obtained with gas and water flowing in the plastic tube 30. FIG. 5B illustrates the stacked signal trace obtained when there was no flow in the plastic tube 30.

EXAMPLE 2

The present invention is useful in the detection of fluid flow behind casing in a borehole traversing an earth formation. An apparatus made in accordance with the present invention is lowered into the borehole through the interior bore of the casing in such a manner that the transducer means are oriented for projecting the acoustic beam radially outward toward the wall of the casing. The apparatus is then operated in a manner similar to that described for the laboratory experiment of Example 1 above to determine the presence of flowing fluid behind the casing, i.e., between the casing and the earth formation. By comparing the stacked signals produced at spaced intervals of time and at varying locations/depths along the borehole, the relative velocities of any fluid flow detected at such times/locations can be determined.

In another embodiment, the method of the present invention includes steps for estimating the velocity of the fluid flowing behind the acoustically reflective structure 14. Referring now to FIGS. 6A-6D and 7, this embodiment is described as follows. The absolute values of a preselected number of difference signals are summed, or "stacked," in n accumulators (corresponding to the third electric circuit 22 shown in FIG. 1). In each individual accumulator, the difference signals (being "stacked") are the result of the subtraction of reflection signals of acoustic pulses fired at T time intervals apart, where T is varied for each accumulator. Preferably, T for each accumulator is a multiple of the T of shortest duration, for reasons which will become apparent. For example, if T for the first accumulator is 50 milliseconds, T for the second accumulator will be 100 milliseconds, and T for the nth accumulator will be (50×n) milliseconds. FIGS. 6A-6D illustrate the "stacked" signals in four accumulators obtained in an experiment in which T=50 milliseconds in FIG. 6A, T=100 milliseconds in FIG. 6B, T=150 milliseconds in FIG. 6C, and T=200 milliseconds in FIG. 6D. At least three accumulators are required to obtain an estimate of the flow velocity. The signals stored in the accumulators in the previous steps are then examined and evaluated as follows:

1) Although not absolutely essential to the method, it is preferred that the entire signal in each accumulator be mathematically smoothed in a transition-preserving algorithm. As one skilled in the art will recognize, a median filter is preferable to a running average in preserving the onset of the scattering signal.

2) Then the signal in the first accumulator is examined to determine if a portion of the signal is above a predetermined baseline. If it is not, then no flow has been detected. If it is, one practicing the method proceeds to the next step.

3) The signal is then examined for a transition from a baseline, indicating a response to the flowing scatterers. Referring to FIGS. 6A-6D, the time of this transition is designated $t_1$. As one skilled in the art will recognize, the time of this transition relates, by way of the acoustic velocity of the reflective structure, to the distance of the flowing fluid from the transducer 12.

4) The signal is then examined for a decline in the response back to the baseline. This point is designated $t_2$ in FIGS. 6A-6D. If no such decline is found, $t_2$ is set to a predetermined value near the end of the trace. As one skilled in the art will recognize, $t_2$ relates—by way of $t_1$, the acoustic velocity of the reflective structure and reverberation effects—to the thickness of the flowing channel.

5) The signal in each accumulator is separately summed (integrated) from $t_1$ to $t_2$. The result from each accumulator summation (integration) is stored in a separate digital memory, designated $S_n$, where n is the number of the accumulator whose signal has been integrated.

Figure 7:
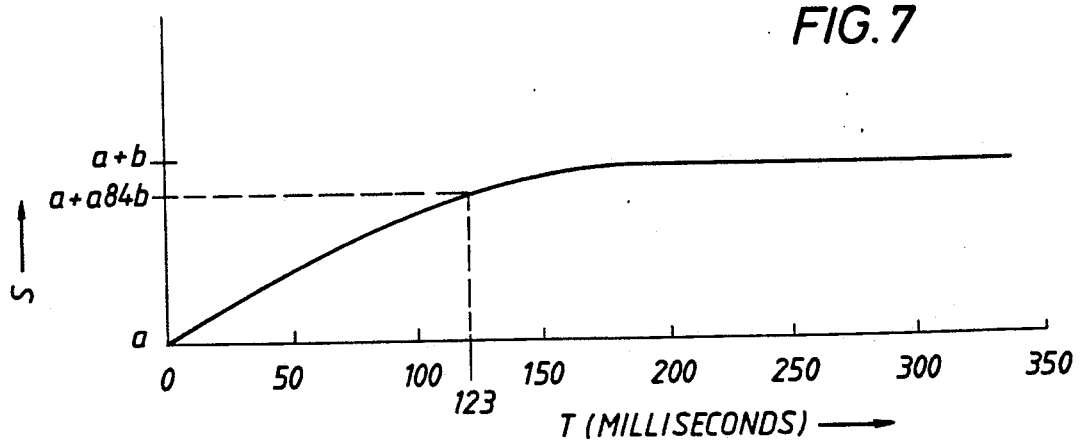
FIG. 7 illustrates a graphical representation of the plot of the summation (integration) of signal traces such as those illustrated in FIGS. 6A through 6D obtained for varying values of "T."

6) The values of S from the previous step are then plotted versus the value of T as shown in FIG. 7. It has been determined that the plot in FIG. 7 is representative of the equation:

$$S = a + b\, erf(VT/W_0)$$

where S=a when T=0, and S=a+b when T approaches infinity; erf is simply an error function; V is the velocity of the scatterers in the flowing fluid; and $W_0$ is the beam half-width of the transducer (determined by the 1/e point).

7) It has been determined that the flow velocity V can then be approximated from the equation:

$$V = W_0/T$$

where T is the value of T at which erf=0.84, which can be determined from the plot generated in the previous step by drawing a line, parallel to the horizontal axis, through the point on the vertical axis which is 0.84 of the way from a to a+b (i.e., at a+0.84b) and reading off the horizontal axis the value of T at which such line intersects the plot of S. FIG. 7 illustrates such a plot in which T=123 milliseconds.

It will be appreciated by those skilled in the art that the foregoing method only provides an approximation of the velocity of the scatterers in the flowing fluid and not the velocity of the fluid itself. However, although the velocity of the fluid and the scatterers contained by the fluid will not always be exactly the same, it will be appreciated that the velocity of the scatterers provides a good estimate of the velocity of the fluid containing them. Accordingly, a method is provided for estimating the velocity of fluid flowing behind an acoustically reflective structure.

It will further be appreciated by those skilled in the art that an apparatus for estimating the velocity of fluid flowing behind an acoustically reflective structure in accordance with the last-described embodiment of the method of the present invention will include a further electric circuit, as shown at 28 in FIG. 1, for controlling the time interval T between pulses fired by the transducer 12 the reflections from which difference signals are derived as described above. In addition, means for performing the summing (integration) operation described above will be provided and can be included, e.g., in the fourth electric circuit 26 shown in FIG. 1.

It will be appreciated by those skilled in the art that the function of the first electric circuit 18 can be performed by a digital oscilloscope having at least two memory channels or a similar circuit. In the experiment described hereinabove under Example 1, a Nicolet ™ Model 4094 oscilloscope with a Model 4570 digitizer was used to store the acoustic reflection (echo) signals generated by the receiving section of the transducer 12.

It will further be appreciated that the subtraction, "stacking," summing (integration), and display functions of the circuits 20, 22, 26, and 24, respectively, can be performed by a digital computer with appropriate peripherals.

Although the present invention has been described in terms of specific embodiments, it is anticipated that alterations and modifications thereof will no doubt become apparent to those skilled in the art. For example, although the application of the present invention to uses in the borehole environment are stressed herein, it will be apparent to those skilled in the art that the present invention will be useful in other situations where it is desirable to determine fluid flow behind an acoustically reflective structure. It is therefore intended that the following claims be interpreted as covering all such alterations and modifications as fall within the true spirit and scope of the invention.

What is claimed is:

1. A method for detecting fluid flow behind an acoustically reflective structure using pulse echo techniques, comprising the steps of:
   (a) generating a high frequency beam of acoustic energy in the form of pulses and directing said beam toward said acoustically reflective structure from a position proximate a first side of said acoustically reflective structure;
   (b) detecting, at a position proximate first said position, acoustic reflections of two of said pulses separated by a short interval of time;
   (c) generating and storing a pair of signal traces plotted against time which are proportional to said acoustic reflections;
   (d) subtracting said pair of signal traces to produce a resultant difference signal trace, whereby substantial variations of amplitude of said difference signal trace is indicative of the presence of fluid flow in proximity to a second side of said acoustically reflective structure opposite said first side; and
   (e) determining from said difference signal trace the presence of fluid flow in proximity to a second side of said acoustically reflective structure opposite said first side.

2. The method for detecting fluid flow behind an acoustically reflective structure as set forth in claim 1 wherein said acoustically reflective structure comprises casing disposed within a borehole traversing an earth formation.

3. A method for detecting fluid flow behind an acoustically reflective structure using pulse echo techniques, comprising the steps of:
   (a) generating a high frequency beam of acoustic energy in the form of pulses and directing said beam toward said acoustically reflective structure from a position proximate a first side of said acoustically reflective structure;
   (b) detecting, at a position proximate first said position, acoustic reflections of a pair of said pulses separated by a short interval of time;
   (c) generating and storing a pair of signal traces plotted against time which are proportional to said acoustic reflections;
   (d) subtracting said pair of signal traces to produce a resultant difference signal trace;
   (e) repeating steps (a) through (d) at least once to produce a preselected number of the difference signal traces of step (d) within a preselected interval of time;
   (f) stacking the preselected number of the difference signal traces of step (e) by summing the absolute values of said difference signal traces to produce a resultant stacked signal trace; and
   (g) determining from said stacked signal trace the presence of fluid flow in proximity to a second side of said acoustically reflective structure opposite said first side.

4. A method for detecting fluid flow behind an acoustically reflective structure using pulse echo techniques and determining the relative velocity of said flow at spaced time intervals, comprising repeating the steps of the method set forth in claim 4 at said spaced time intervals followed by the further step of comparing the resultant stacked signal traces of step (f).

5. An apparatus for detecting fluid flow behind an acoustically reflective structure using pulse echo techniques, comprising:
   (a) a transducer for generating a high frequency beam of acoustic energy in the form of pulses and directing said beam toward said acoustically reflective structure from a position proximate a first side of said acoustically reflective structure;
   (b) a transducer for detecting, at a position proximate first said position, acoustic reflections of a pair of said pulses separated by a short interval of time, and generating electrical signals which are a function of said acoustic reflections;
   (c) a first electric circuit, coupled to the detecting transducer of element (b), for recording a pair of signal traces of said electrical signals plotted against time;
   (d) a second electric circuit, coupled to the first electric circuit, for subtracting said pair of signal traces to produce a resultant difference signal trace; and
   (e) a display coupled to the second electric circuit.

6. The apparatus of claim 5 wherein the transducers of element (a) and element (b) comprise a single transducer.

7. The apparatus of claim 5 wherein the transducers of element (a) and element (b) comprise separate transducers.

8. The apparatus of claim 5, wherein said display comprises means for producing a visual representation of said difference signal trace from which the presence of fluid flow in proximity to a second side of said acoustically reflective structure opposite said first side can be determined.

9. The apparatus of claim 5, further comprising a third electric circuit, coupled to the second electric circuit, for stacking said difference signal traces by summing the absolute values of said difference signal traces to produce a resultant stacked signal trace and said display comprising means for producing a visual representation of said stacked signal trace from which the presence of fluid flow in proximity to a second side of said acoustically reflective structure opposite said first side can be determined.

10. An apparatus for detecting fluid flow behind an acoustically reflective structure using pulse echo techniques and determining the relative velocity of said flow at spaced intervals, comprising:
   (a) a transducer for generating a high frequency beam of acoustic energy in the form of pulses and directing said beam toward said acoustically reflective structure from a position proximate a first side of said acoustically reflective structure;

(b) a transducer for detecting, at a position proximate first said position, acoustic reflections of a pair of said pulses separated by a short interval of time, and generating electrical signals which are a function of said acoustic reflections;

(c) a first electric circuit, coupled to the detecting transducer of element (b), for recording a pair of signal traces of said electrical signals plotted against time;

(d) a second electric circuit, coupled to the first electric circuit, for subtracting said pair of signal traces to produce a resultant difference signal trace;

(e) a third electric circuit, coupled to the second electric circuit, for stacking said difference signal traces by summing the absolute values of said difference signal traces to produce a resultant stacked signal trace;

(f) a fourth electric circuit, coupled to the third electric circuit for recording a plurality of said stacked signal traces generated at spaced intervals of time; and (g) a display, coupled to the fourth electric circuit, for producing a visual representation of last said stacked signal traces from which a comparison of said signal traces can be made to determine the relative velocities of fluid flow in proximity to a second side of said acoustically reflective structure opposite said first side at said spaced intervals of time.

11. A method for detecting and estimating the velocity of fluid flow behind an acoustically reflective structure using pulse echo techniques, comprising the steps of:

(a) generating a high frequency beam of acoustic energy in the form of pulses and directing said beam toward said acoustically reflective structure from a position proximate a first side of said acoustically reflective structure;

(b) detecting, at a position proximate first said position, acoustic reflections of two of said pulses separated by a short interval of time T;

(c) generating and storing a pair of signal traces plotted against time which are proportional to said acoustic reflections;

(d) subtracting said pair of signal traces to produce a resultant difference signal trace;

(e) repeating steps (a) through (d) at least once to produce a preselected number of the difference signal traces of step (d) within a preselected interval of time;

(f) stacking the preselected number of the difference signal traces of step (e) by summing the absolute values of said difference signal traces to produce a resultant stacked signal trace;

(g) summing the amplitude values of the stacked signal traces obtained in step (f) from a time $t_1$ to a time $t_2$, where $t_1$ is the time at which the amplitude value rises above a baseline and $t_2$ is the time at which the amplitude value declines toward said baseline;

(h) repeating steps (a) through (g) a preselected number of times for varying values of T in step (b) and plotting the result of step (g) versus the value of T; and (i) determining from an analysis of the plot produced in step (h) an estimate of the velocity of said fluid flowing behind said acoustically reflective structure.

12. The method of claim 11 for determining from said analysis in step (i) of said plot produced in step (h) the estimate of the velocity of said fluid behind an acoustically reflective structure, wherein:

(a) letting said summing amplitudes values of step (g) equal a value S and said plot of said S versus time be representative of the equation, $$S = a + b\, erf(VT/Wo)$$

where S=a when T=0, and S=a+b when T approaches infinity, erf is an error function, V is the velocity of the fluid, Wo is the beam half-width of a transducer determined by the 1/e point; and (b) determining from an analysis of said plot the flow velocity said fluid by using the equation, $$V = Wo/T$$

where T is the value of T at which erf=0.84 on said plot.

* * * * *